July 16, 1957 D. B. COLE Plant Pat. 1,619
HONEY LOCUST TREE
Filed Aug. 16, 1955
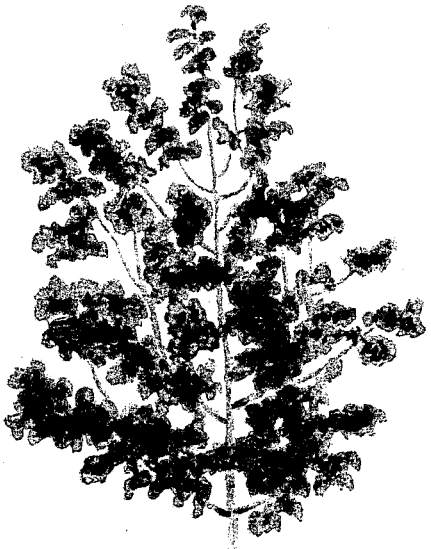
Fig. 1
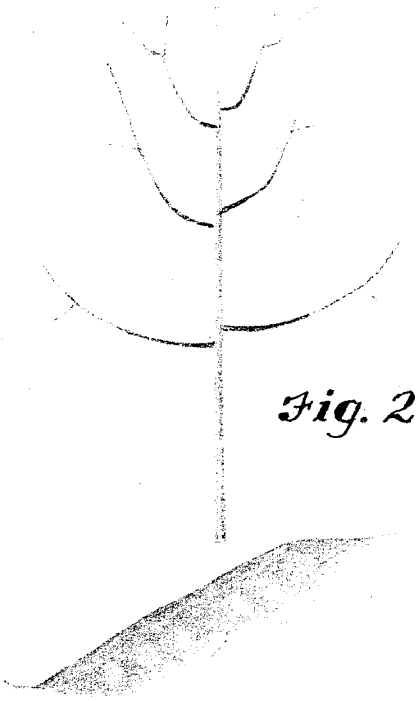
Fig. 2
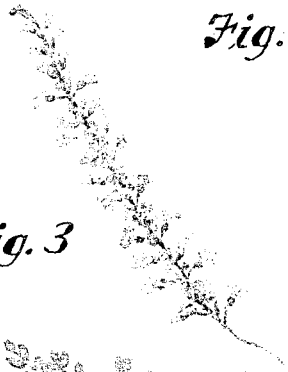
Fig. 3
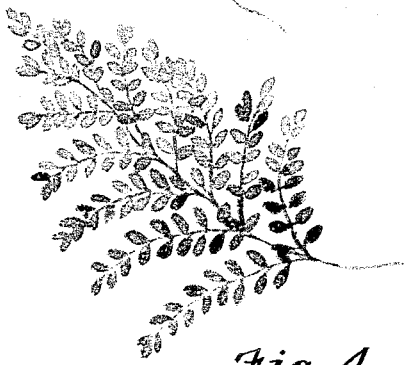
Fig. 4
Fig. 5
WITNESS
Addison E. Avery
INVENTOR
DAVID BARRETT COLE
BY Oberlin & Limbach
ATTYS.

United States Patent Office

Plant Pat. 1,619
Patented July 16, 1957

1,619

HONEY LOCUST TREE

David Barrett Cole, Mentor Township, Lake County, Ohio, assignor to The Cole Nursery Company, Painesville, Ohio, a corporation of Ohio Application August 16, 1955, Serial No. 528,857

1 Claim. (Cl. 47—59)

The present invention relates to a new and distinct variety of honey locust tree, *Gleditsia triacanthos* L., var. *inermis,* originated by me, having a novel habit of growth and other distinguishing characteristics as will be hereinafter more particularly pointed out.

I have propagated my new thornless honey locust tree at Painesville, Ohio, asexually by budding, and the tree can be very readily propagated in this manner, perpetuating all of its original character. The original parent specimen was a seedling grown by me at the same location. Such original parent specimen was discovered by me in a plantation of approximately 10,000 thornless honey locust seedlings grown by me from seed from selected parent trees exhibiting some tendency toward the desired characteristics.

As to habit of growth, my new and distinct variety of honey locust tree is characterized by having a strong, sturdy, straight trunk, upright spreading branches and very dark green leaflets. In two to five year specimens, the branches are well spaced and uniformly arranged, the growth habit suggesting a medium to large tree at maturity, but one of noticeable upright habit compared with the wide spreading nature of the species and the *inermis* variety.

Referring to the drawing:

Fig. 1 shows my new honey locust tree six years after budding on a two-year seedling;

Fig. 2 illustrates the manner of branching of my new tree, the branches emerging from the trunk at wide angles thereto and then turning upward;

Fig. 3 shows buds and blooms of my new tree; these, however, have no apparent exceptional characteristics;

Fig. 4 shows a branchlet, the outermost pinnae of which are faintly touched with bronze (see also Fig. 1), this being usual but not ubiquitous, depending somewhat on the season and growing conditions; and Fig. 5 shows the fruit which, when produced, appears to be the typical pod of the common honey locust. To date it has been produced extremely sparingly and the tree seems to be very nearly seedless.

The color identifications given below are with reference to the "Horticultural Colour Chart," published by the British Colour Council in collaboration with The Royal Horticultural Society (Great Britain, Henry Stone & Son, Ltd.).

As illustrated by the drawing, the branches emerge from the trunk at a relatively wide angle, mostly 60° to 90° but quickly turn upward, giving an upward branching appearance to the tree. The angle of emergence of the branches from the trunk is such as to assure relatively strong crotches. The branches are well spaced and emerge in all directions from the trunk, giving no indication of a one-sided or flat-branch arrangement often characteristic of the species. The branches are sturdier than those of the common thornless honey locust. The bark on the young growing branches near their tips is Scheeles Green 860/3 shading to Scheeles Green 860 progressively along the branch and gradually and finally becoming Spinach Green o960 toward the trunk, and strikingly lenticellate. The trunks are essentially free from thorns, but rarely a few short, stubby thorns are found on vigorous, side branches. The color of the bark on the trunk of a young specimen (e. g. seven years of age) is Willow Green ooo862/2 and ooo862/1 underlaid dull brownish.

The mature leaves are 15 to 27 cm. long and mostly bipinnate. The bipinnate leaves have 10 to 16 pinnae, mostly 12 to 14, and near the tips of the branchlets the leaflets are Lettuce Green 861/2 graduating and shading inward toward the stem or trunk through Scheeles Green 860/3 to 860/2 to Spinach Green o960/2. The mature leaflets are Parsley Green oo962 so that the foliage of the entire tree appears this color at the end of the season. The extreme growing tips of the foliage frequently contain faint Garnet Brown oo918/3. The leaf rachis is grooved and hairy, mostly at the groove. Pinnate leaves with 20 to 30 oblong-lanceolate leaflets, mostly 2.0 to 3.5 cm. long, dark green on both sides, slightly hairy below, most on the midrib, and with crenate-serrulate margins. The leaves are spaced somewhat closer and the leaflets on the bipinnate leaves are larger than those on the common thornless honey locust. These characteristics lend to a more compact habit. The newly formed leaves show bronze tips and are attractive.

The flowers of my new variety of honey locust are mostly male, but slightly polygamous. The flowers are borne in racemes, with about ten percent of the racemes showing one female flower at the tip of the raceme, the other flowers in the raceme being male. The racemes are 4 to 8 cm. in length and densely set with buds and flowers, the buds being Fern Green o862 and the florets being Citron Green. The racemes are 10 to 15 mm. in diameter; the peduncles 5 to 12 mm. in length; the pedicels 1 to 3 mm. in length; and the styles 3 to 4 mm. in length. The rachis and pedicels are densely tomentose; the petals and calyx lobes are appressed to the stamens and are cup shaped. The flowers open somewhat earlier than normal but are not otherwise exceptional.

The fruit, when sparingly produced, is the typical pod of the common honey locust. Such pod (Fig. 5) may be 5 inches long, ⅞ inch wide, and have 4 seeds with 2 blanks. The color ranges from Sap Green 62/2 to Uranium Green 63/2 with the upper edge fusing into and overlaid with Garnet Brown oo918/3. While insufficient fruit has set to generalize, it is expected that the pod length may vary between 5 and 8 inches and the width between ⅞ and 1¼ inches. The number of seeds may range from 4 to 10. Judging from the trees to date, however, they are substantially seedless.

I claim:

A new and distinct variety of substantially thornless honey locust tree, *Gleditsia triacanthos* L., var. *inermis,* having a strong, sturdy, straight trunk with well spaced and uniformly arranged branches, said branches emerging from the trunk at a relatively wide angle, but then quickly turning upward, giving an upright branching appearance to the tree, the mature leaflets being dark green.

No references cited.